United States Patent
Wall Warner et al.

(10) Patent No.: US 10,909,215 B2
(45) Date of Patent: Feb. 2, 2021

(54) METHOD AND SYSTEM FOR CODIFICATION, TRACKING, AND USE OF INFORMED CONSENT DATA FOR HUMAN SPECIMEN RESEARCH

(71) Applicant: GLOBAL SPECIMEN SOLUTIONS, INC., Raleigh, NC (US)

(72) Inventors: Amelia Wall Warner, Raleigh, NC (US); Mark Anthony Collins, Raleigh, NC (US)

(73) Assignee: Global Specimen Solutions, Inc., Raleigh, NC (US)

(*) Notice: Subject to any disclaimer, the term of this patent is extended or adjusted under 35 U.S.C. 154(b) by 0 days.

(21) Appl. No.: 15/651,357

(22) Filed: Jul. 17, 2017

(65) Prior Publication Data

US 2017/0316163 A1    Nov. 2, 2017

Related U.S. Application Data

(63) Continuation of application No. PCT/US2016/062724, filed on Nov. 18, 2016.

(Continued)

(51) Int. Cl.
*G16H 10/40* (2018.01)
*G06F 19/00* (2018.01)
(Continued)

(52) U.S. Cl.
CPC .......... *G06F 19/324* (2013.01); *G06N 20/00* (2019.01); *G06Q 50/22* (2013.01); *G16H 10/40* (2018.01); *G16H 50/30* (2018.01); *G16H 10/20* (2018.01)

(58) Field of Classification Search
CPC ................................. G06Q 50/22–24
See application file for complete search history.

(56) References Cited

U.S. PATENT DOCUMENTS 8,433,344 B1    4/2013  Virga
2003/0033168 A1*  2/2003  Califano ............... G06F 19/322
                                                                                     705/3

(Continued)

FOREIGN PATENT DOCUMENTS

WO    2013/106326 A1    7/2013

OTHER PUBLICATIONS

PCT, International Search Report and Written Opinion for PCT/US2016/062724 dated May 4, 2017.

(Continued)

*Primary Examiner* — Robert A Sorey
(74) *Attorney, Agent, or Firm* — Kilpatrick Townsend & Stockton LLP (57) ABSTRACT

The subject matter described herein includes methods, systems, and computer program products for codification, tracking, and use of informed consent data for human specimen research. According to one method, an informed consent document is codified and consent rules are attached to a specimen. The consent rules and any changes to the consent rules are tracked. Allowed use analysis of the specimen and associated data is performed and a regulatory intelligence knowledgebase (RIK) is provided that includes global regulations data derived from proprietary and public sources. A consent document is automatically generated using the codified informed consent document and the RIK.

12 Claims, 6 Drawing Sheets

Related U.S. Application Data (60) Provisional application No. 62/256,756, filed on Nov. 18, 2015.

(51) Int. Cl.
*G06N 20/00* (2019.01)
*G06Q 50/22* (2018.01)
*G16H 50/30* (2018.01)
*G16H 10/20* (2018.01)

(56) References Cited

U.S. PATENT DOCUMENTS

| | | |
|---|---|---|
| 2003/0139942 A1 | 7/2003 | Rakshit et al. |
| 2003/0154105 A1 | 8/2003 | Ferguson |
| 2003/0212578 A1 | 11/2003 | Link et al. |
| 2005/0203773 A1 | 9/2005 | Soto et al. |
| 2005/0228622 A1 | 10/2005 | Jacobi |
| 2009/0210388 A1* | 8/2009 | Elson ............... G06F 17/30241 |
| 2013/0151280 A1* | 6/2013 | Thiers ................... G06Q 50/22 705/2 |
| 2013/0297626 A1* | 11/2013 | Levi .................. G06K 9/00442 707/754 |
| 2015/0039327 A1 | 2/2015 | Pal |
| 2015/0178644 A1* | 6/2015 | Oleson ............... G06Q 10/0635 705/2 |
| 2015/0302536 A1* | 10/2015 | Wahl ..................... G06Q 50/00 705/2 |
| 2016/0070758 A1* | 3/2016 | Thomson ............... G16H 10/60 707/781 |
| 2017/0098051 A1* | 4/2017 | Balram ................. G16H 40/67 |
| 2017/0116373 A1* | 4/2017 | Ginsburg ............... G16H 40/20 |

OTHER PUBLICATIONS

SG11201803784W, "Written Opinion", dated Jul. 3, 2019, 9 pages.
"Integrating the Healthcare Enterprise IHE IT Infrastructure (ITI) Technical Framework vol. 1 (ITI TF-1) Integration Profiles Revision 11.0—Final Text", Available online at, URL:http://www.ihe.netjuploadedFilesjDocuments/ITI/IHEITI_TF_Rev11.0_Vol1_FT_2014-09-23.pdf, Chapter 19, Sep. 23, 2014, 304 pages.
Kosa, T., "Towards Measuring Privacy", Available online at: https://ir.library.dc-uoit.cajbitstream/10155/609/1/KosaTracy%20Ann.pdf, Apr. 15, 2015, 213 pages.
CA Application No. 3,004,479, "Office Action", dated Mar. 6, 2019, 5 pages.
CA Application No. 3,004,479, "Office Action", dated Apr. 22, 2020, 6 pages.
EP Application No. 16867205.3, "Extended European Search Report", dated Jun. 17, 2019, 10 pages.
JP Application No. 2018-526516, "Office Action", dated Feb. 18, 2020, 7 pages.
SG Application No. 11201803784W, "Further Written Opinion", dated May 12, 2020, 7 pages.

\* cited by examiner

METHOD AND SYSTEM FOR CODIFICATION, TRACKING, AND USE OF INFORMED CONSENT DATA FOR HUMAN SPECIMEN RESEARCH

CROSS-REFERENCE TO RELATED APPLICATION

This application is a continuation of International Patent Application Serial No. PCT/US16/62724, filed Nov. 18, 2016, 756 titled "A Method and System for Codification, Tracking, and Use of Informed Consent Data For Human Specimen Research", which claims the benefit of priority of U.S. provisional patent application No. 62/256,756 titled "A Method and System for Codification, Tracking, and Use of Informed Consent Data For Human Specimen Research" filed on Nov. 18, 2015, which applications and their contents are incorporated herein by reference.

BACKGROUND

Field of the Invention

The present invention relates to consent data for human specimen research, and more specifically, to methods and systems for codification, tracking, and use of informed consent data for human specimen research.

Description of Related Art

Human specimen research is a key step on the path to precision medicine. The acquisition, analysis, and storage of specimens obtained from human subjects during the course of clinical trials, research studies, patient registries, and institutional biobanks is an enabler of the search for new medicines and diagnostics. Specimens collected during the course of clinical trials are highly annotated and offer a rich resource for both the trial outcome as well as future biomedical research (FBR).

Regulation, in the form of informed consent, governs acquisition, use, analysis, and destruction of specimens and data. Patients and study subjects sign informed consent to allow the collection, storage, use and data related to specimens. Capturing the informed consent and tracking it in relation to the specimen and the data about specimens is key to regulatory compliance for both trial activities and future biomedical research. The consequences of failing to adequately track consent can be severe in terms of regulatory fines (dollars), loss of trust of the organization using specimens or data without proper knowledge of consent, and the loss of the ability to use biological resources to drive future biomedical research.

Accordingly, a need exists for improved methods and systems for managing informed consent data for human specimen research.

BRIEF SUMMARY OF THE INVENTION

The subject matter described herein includes methods, systems, and computer program products for codification, tracking, and use of informed consent data for human specimen research. According to one embodiment of the present invention, a method for codification, tracking, and use of informed consent data for human specimen research may comprise codifying, by a server, an informed consent document; attaching, by the server, consent rules to a specimen; tracking, by the server, the consent rules and any changes to the consent rules; performing, by a server, allowed use analysis of the specimen and associated data; and automatically generating, by a server, a consent document using the codified informed consent document and a regulatory intelligence knowledgebase (RIK), wherein the RIK includes global regulations data derived from proprietary and public sources.

According to some embodiments, codifying, by a server, an informed consent document may further include using machine learning to translate the informed consent document into a set of classes, where the classes encode the informed consent document into a machine actionable format or set of rules, wherein the rules define what the patient has consented to be done with the specimen and the data.

According to some embodiments, codifying, by a server, an informed consent document may be linked to and performed based upon prevailing global, country, regional, and local regulations in force at the time of codification.

According to some embodiments, attaching, by a server, consent rules to a specimen may include linking a consent profile to the specimen and to the data derived from the specimen.

According to some embodiments, attaching, by a server, consent rules to a specimen may be performed on a patient, collection site, sample type, country, and regional basis.

According to some embodiments, tracking, by a server, the consent rules may further include dynamically tracking changes in restrictions regarding what can be done to the specimen and/or whether the patient withdraws consent.

According to some embodiments, performing, by a server, allowed use analysis may further include providing rules-based querying for specific consent profiles.

According to some embodiments, performing, by a server, allowed use analysis may further include providing a risk assessment from a consent perspective.

According to some embodiments, the RIK may be used to create risk-based models for specimen and data collection.

According to some embodiments, the RIK may further inform the risk-based models by learning behaviors of internal review boards (IRBs), ethics committees, health authorities, and other bodies involved in consent approval.

According to some embodiments, the behaviors may include one or more of: performance, speed of approval, interpretation of local and global regulations, level of cautiousness, and trends over time.

According to some embodiments, automatically generating, by a server, a consent document may further include generating the consent document based on an outline of desired consent, categories of consent needed, and regulations.

According to some embodiments, a global consent landscape portal may provide a global consent landscape analysis.

According to some embodiments, the global consent landscape portal may include visual indicators that provide a rapid visual assessment or risk, wherein the visual indicators or risk are overlaid on a map, together with filters to allow interactive visualization of different risk categories.

According to yet other embodiments of the present invention, a system for codification, tracking, and use of informed consent data for human specimen research may comprise a regulatory intelligence knowledgebase (RIK), wherein the RIK includes global regulations data derived from proprietary and public sources. The system may further comprise a server with a processor and a memory configured to codify an informed consent document, attach consent rules to a specimen, track the consent rules and any changes to the consent rules, perform allowed use analysis of the specimen and associated data, and automatically generate a consent document using the codified informed consent document and the RIK.

According to yet other embodiments of the present invention, a computer program product for codification, tracking, and use of informed consent data for human specimen research may comprise computer code for codifying an informed consent document, computer code for attaching consent rules to a specimen, computer code for tracking the consent rules and any changes to the consent rules, computer code for performing allowed use analysis of the specimen and associated data, and computer code for automatically generating a consent document using the codified informed consent document and a regulatory intelligence knowledgebase (RIK), wherein the RIK includes global regulations data derived from proprietary and public sources.

DETAILED DESCRIPTION

The subject matter described herein includes systems and methods designed to manage the codification, tracking and use of informed consent data for human specimen research. Generally, pre-existing informed consent documents may be reverse engineered to generate a new and more useful "codified" informed consent document. This codified informed consent document may be machine readable and machine actionable so that it can be stored and retrieved in an electronic database. When a patient provides a specimen, the system may create a consent profile for the patient that links various information to the specimen. Thereafter, it is easier to track the patient's consent and any changes (e.g., withdrawal of consent) in order to ensure that organizations are managing specimens and their associated data in compliance with the applicable consent rules and regulations. Analytics can provide rapid assessments of risk or other metrics based on various granular searches using an interactive visual portal, such as a webpage or interactive application. Finally, the system may be used to help automatically generate new consent documents based on desired specifications such that the consent documents can be assembled very rapidly and in an automated manner by people without legal training.

Figure 1:
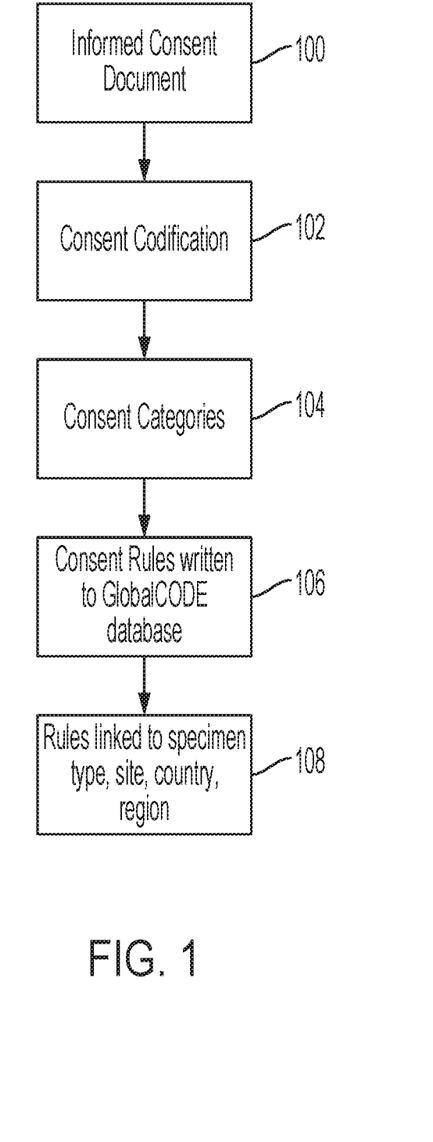
FIG. 1 is a flow chart illustrating steps of an example consent codification process for codification, tracking and use of informed consent data for human specimen research according to an embodiment of the present invention.

Referring now to FIG. 1, a flow chart illustrating steps of an example consent codification process of an informed consent document according to an embodiment of the present invention is shown. At step 100, an informed consent document may be received. Informed consent forms or documents may explain to the patient what permissions they can consent to for the use of the specimens and data, such documents are built during the study setup and reviewed and approved by an internal review board (IRB). The informed consent form may be written with global and local (country) regulations in mind as well as site specific needs.

At step 102, a combination of expert assessment, natural language processing and machine learning may be used to translate or "reverse engineer" the meaning of the informed consent document into a set of classes. These classes may encode the informed consent document into a machine actionable format or set of rules. The rules in turn may define what the patient has consented for in terms of what can be done with their specimens and data. Codification may be an early step in the process of tracking consent. Traditional methods that merely link the signed consent document to the specimen do not permit automated assessment of the consent and, therefore, are cumbersome because they rely on a human to read and interpret the consent and take an action.

At step 104, one or more consent categories may be determined. Codification may be carried out based upon prevailing global, country, regional and local regulations and, therefore, may be linked to the regulations in force at the time of codification. In this way, specimens collected for example in 2005 under that years' prevailing rules may be used even if regulations changed in 2007 to restrict use of certain forms of analysis on those specimens.

At step 106, the consent rules may be written to a database. For example, the codified informed consent documentation may be stored in an electronic database in one or more machine-readable formats for easier processing. Details of the database and its use will be described in greater detail below.

At step 108, the consent codification process may also include attaching consent rules to the specimen. For example, the system may integrate the consent rules together with the specimen and data on a patient, collection site, sample type, country and regional basis. In this way, the patient's consent "profile" may be irrevocably linked to the specimen and the data derived from that specimen. Furthermore, any derivatives of that parent specimen of any type may also be linked to the consent profile.

Figure 2:
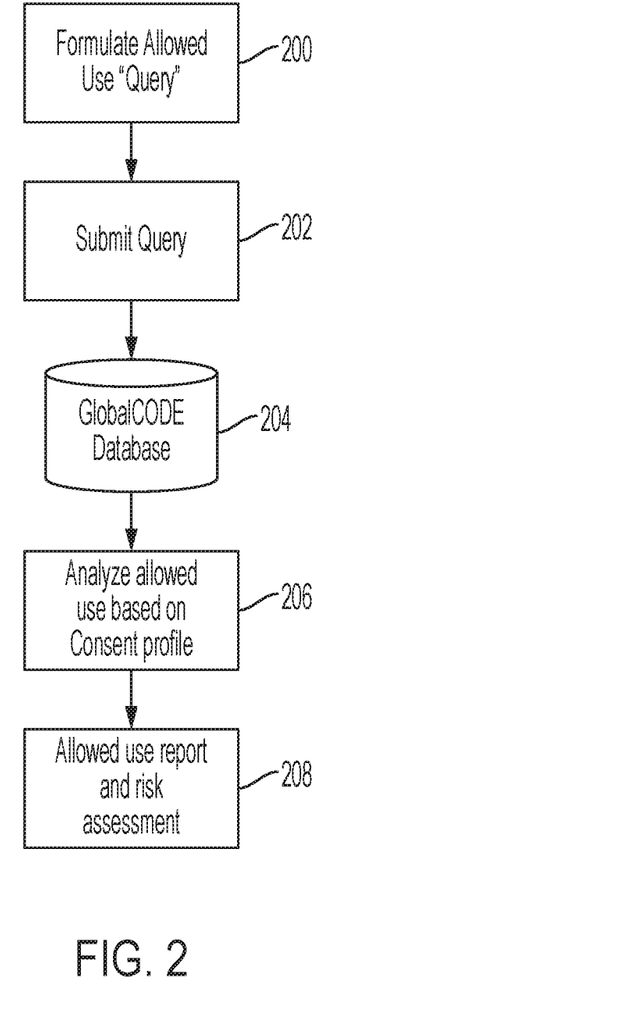
FIG. 2 is a flow chart illustrating steps of an example consent tracking process for codification, tracking and use of informed consent data for human specimen research according to an embodiment of the present invention.

Referring now to FIG. 2, is a flow chart illustrating steps of an example consent tracking process for codification, tracking and use of informed consent data for human specimen research according to an embodiment of the present invention is shown. Consent rules and any changes to those rules, for example, changes in restrictions on what can be done to the specimen, or if the patient withdraws consent may be tracked. Dynamic consent tracking may ensure that organizations using specimens and data are always in compliance.

At step 200, an allowed use query may be formulated and, at step 202, the query may be submitted to a database 204. For example, the query may include, "What are the destruction dates for the tissue specimens from patient X?"

At step 206, the allowed use case may be analyzed based on consent use profile. For example, the consent use profile may indicate that tissue samples for patient X must be destroyed by December 2015 but can be used for FBR up to that date.

At step 208, an allowed user report and risk assessment may be generated and provided.

Figure 3:
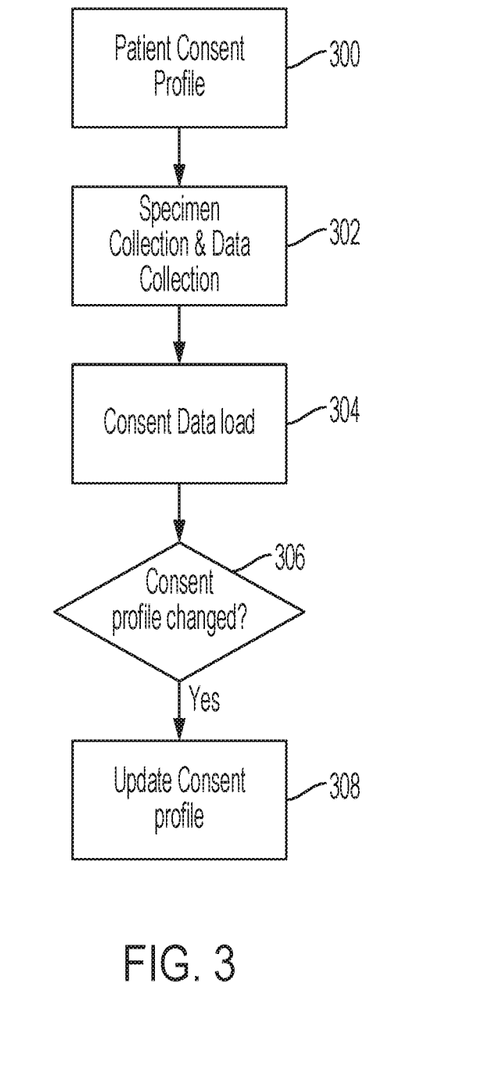
FIG. 3 is flow chart illustrating steps of an example allowed use analysis process for codification, tracking and use of informed consent data for human specimen research according to an embodiment of the present invention.

Referring now to FIG. 3, flow chart illustrating steps of an example allowed use analysis process for codification, tracking and use of informed consent data for human specimen research according to an embodiment of the present invention is shown. Some embodiments of the present invention may permit rapid determination of allowed use of specimens and data and the rule based querying for specific consent profiles. For example, "tissue samples available for genomic analysis from Brazil." The subject matter described herein may also provide a "risk assessment" from a consent perspective when specimens and data are being queried or browsed during analyses, inventory searches, cohort creation, sample acquisition from third parties and other interaction where an understanding of allowed usage risk is important.

At step 300, a patient consent profile may be created. A patient consent profile may indicate all details regarding what a patient has consented to for his or her specimens and associated data. Specimen collection and data collection may also be performed at step 300. This may include collecting tissue samples, biographical or medical information, or similar items obtained from human subjects during, for example, the course of clinical trials, research studies, patient registries, or diagnostics.

Further, at step 300, the consent data is loaded and, at step 306, it is determined whether the consent profile has changed. If so, the consent profile is updated at step 308. This may include updating the consent profile when the patient withdraws their consent, or vice versa, as well as adjusts any details regarding their consent (e.g., time, place, manner).

Figure 4A:
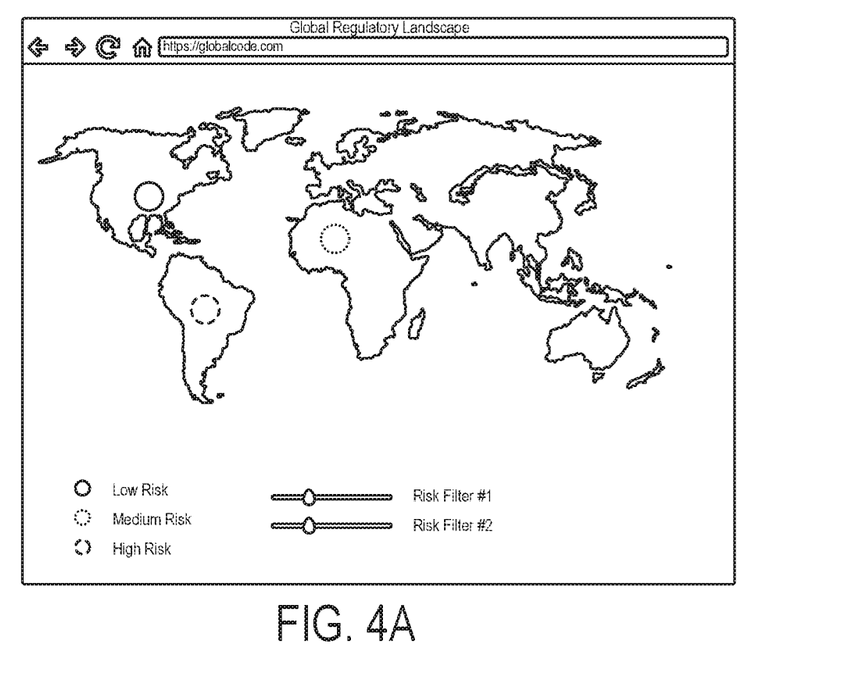
FIGS. 4A and 4B are depictions of an example global consent landscape portal for codification, tracking, and use of informed consent data for human specimen research according to an embodiment of the present invention.
Figure 4B:
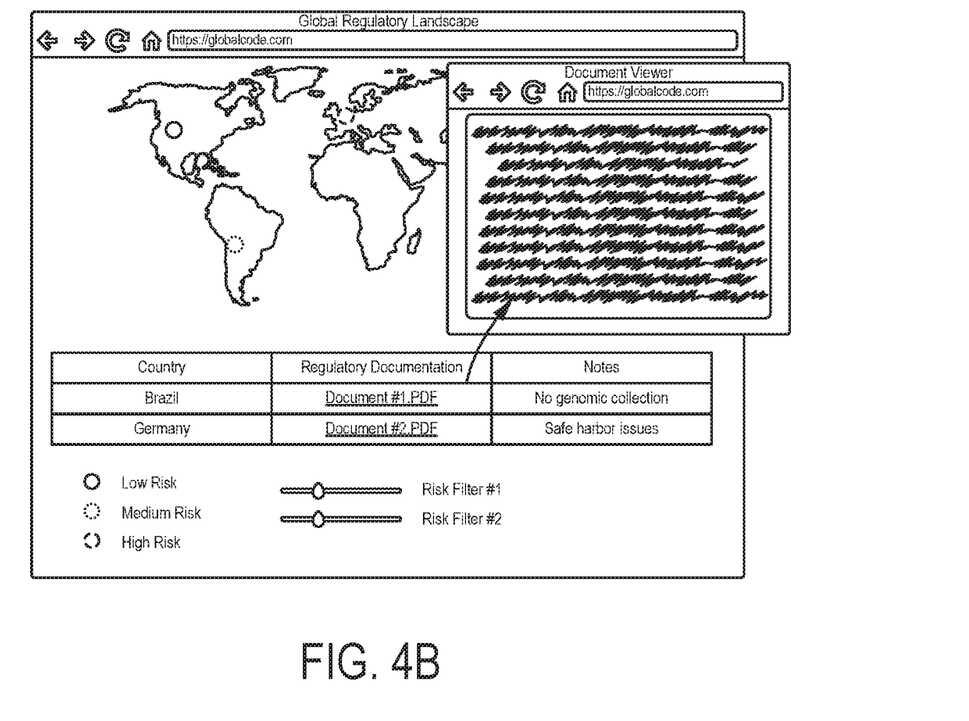

Referring now to FIGS. 4A and 4B, wireframes illustrating an example global consent landscape portal for codification, tracking and use of informed consent data for human specimen research according to an embodiment of the present invention is shown. Some embodiments of the present invention may provide a global consent landscape analysis, allowing organizations to rapidly determine the risk of performing trials, collecting specimens and enrolling patients form a consent perspective. Visual indicators may provide rapid visual assessment of risk. The global landscape analysis may be represented in the form of a map with indicators of risk overlaid on the map, together with filters to allow interactive visualization of different risk categories.

The global consent landscape analysis may contain links to further information about the consent landscape, including the actual written consent regulations, as well as "intelligence on each location to help inform the risk assessment derived from the Regulatory Intelligence Knowledgebase (RIK). For example, as can be seen from FIG. 4A, a geographical map is displayed with colors-coded indicators of low, medium, and high risk. One or more risk filters may be adjusted by using the risk filter sliders in order to provide a lower and upper risk limit to be displayed on the map.

In FIG. 4B, specific regulatory information may be linked in the form of PDF files, for example, which may be used to display relevant regulatory intelligence linked in the database.

Figure 5:
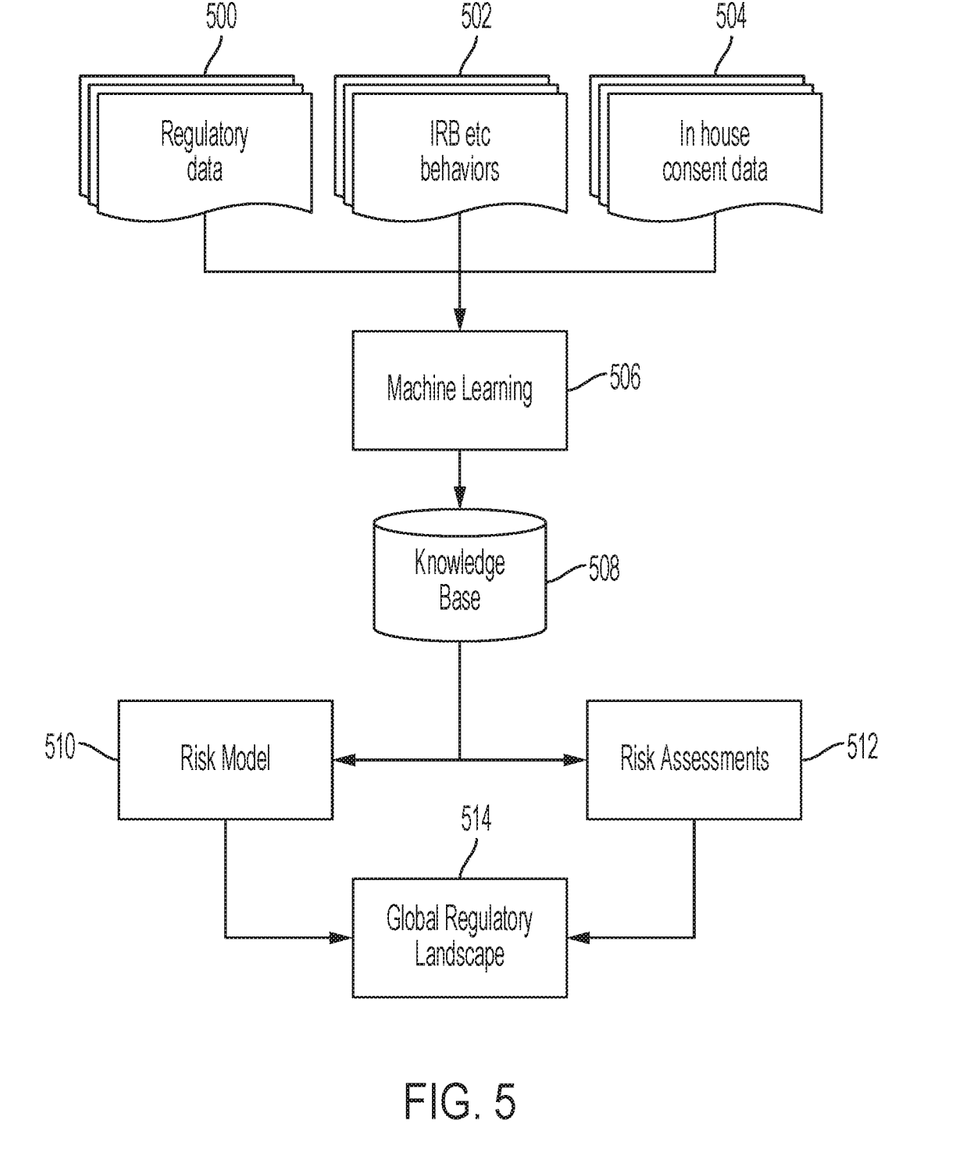
FIG. 5 is a block diagram illustrating example components and functions associated with a regulatory intelligence knowledgebase for codification, tracking and use of informed consent data for human specimen research according to an embodiment of the present invention.

Referring now to FIG. 5, a block diagram illustrating example components and functions associated with a regulatory intelligence knowledgebase for codification, tracking and use of informed consent data for human specimen research according to an embodiment of the present invention is shown.

Some embodiments of the present invention may use data derived from multiple sources, both proprietary and public to build a knowledge base of global regulations. For example, regulatory data 500, IRB behaviors 502, and in-house consent data 504 may be processed at machine learning step 506. The RIK 508 may use machine learning 506 and statistical approaches to provide regulatory intelligence to inform decision making and forecast the risk of, for example, trying to collect genomic samples in a region of Germany.

The RIK 508 may also be used, together with the analytics to create risk based models for specimen and data collection. Such models may be used as decision support tools for example when writing and negotiating consent in different regions.

The RIK 508 may also learn behaviors of IRB's, ethics committees, Health Authorities and other bodies involved in consent approval which further informs the risk-based models. For example, the RIK 508 may inform risk model 510 and risk assessments 512, which in turn informs global regulatory landscape 514. Such behaviors such as, but not limited to, performance, speed of approval, interpretation of local and global regulations, whether overly cautious or restrictive, trends over time and others.

Figure 6:
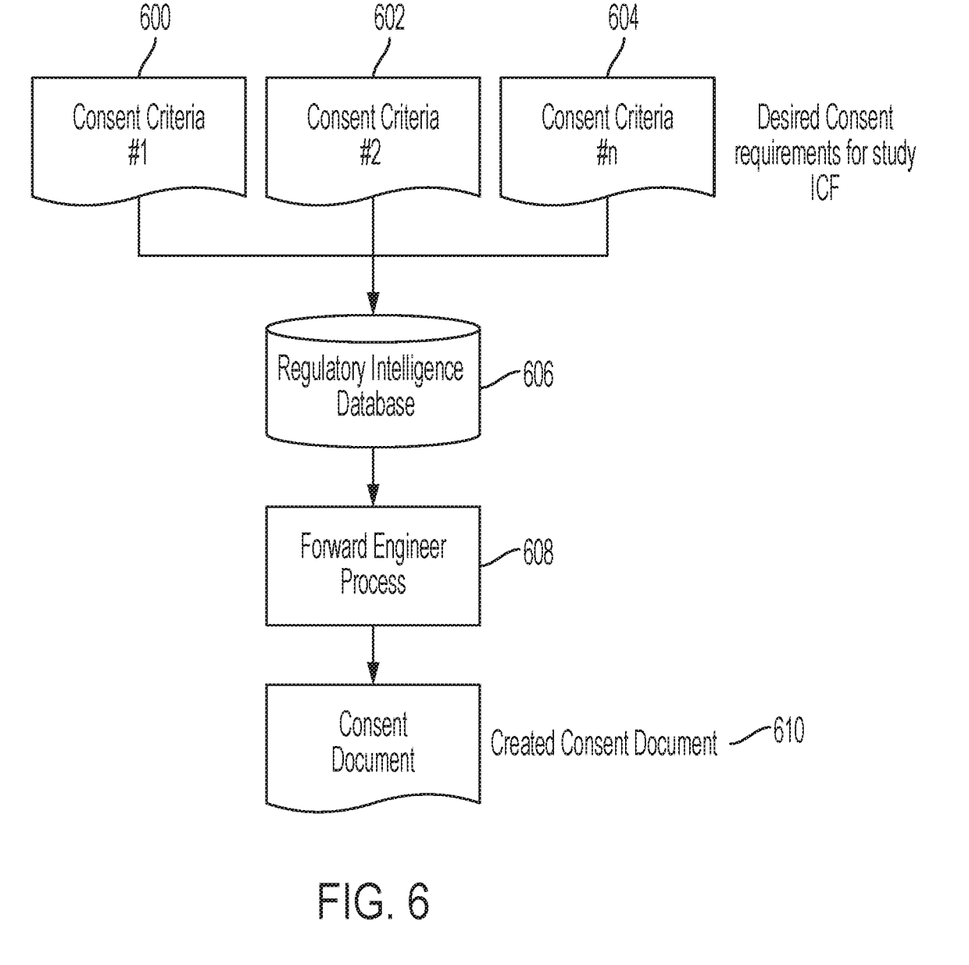
FIG. 6 is a block diagram illustrating example components and functions associated with a machine-driven informed consent builder for codification, tracking and use of informed consent data for human specimen research according to an embodiment of the present invention.

Referring now to FIG. 6, a block diagram illustrating example components and functions associated with a machine-driven informed consent builder for codification, tracking, and use of informed consent data for human specimen research according to an embodiment of the present invention is shown. Some embodiments of the present invention may use the RIK 606 and the codification database to "forward engineer" a consent document based on an outline of the desired consent, categories of consent needed and regulations etc. Such consent documents can be assembled very rapidly and in an automated manner by people without legal training. Consent documents built in this way benefit from the assembled corpus of consent information in the RIK 606.

For example, a first consent criteria 600, a second consent criteria 602, and a third consent criteria 604 may be input into regulatory intelligence database 606. The RIK 606 may be used for forward engineer process 608.

At step 610, a consent document is automatically generated that is based on an outline of desired consent, categories of consent needed, and regulations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter situation scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   codifying, by a server, a pre-existing informed consent document into a machine actionable set of rules using machine-learning, natural language processing, and expert assessment, wherein the machine actionable set of rules defines what a patient has consented to be done with a specimen and data derived from the specimen in at least some of a plurality of locations;
   storing within non-transitory memory in the server, the machine actionable set of rules;
   tracking, by the server, changes to the machine actionable set of rules;
   automatically generating, by the server, a new consent document based at least in part on global regulations data derived from proprietary and public sources, by using the machine actionable set of rules with any changes and a machine-learning regulatory intelligence knowledgebase (RIK), wherein the machine-learning RIK includes the global regulations data; and
   interactively displaying, using analytics of consent approval, visual risk indicators for collection of the specimen in association with the new consent document as visually corresponding to the plurality of locations on a map.

2. The method of claim 1, wherein the codifying is linked to and performed based upon prevailing global, country, regional, and local regulations in force at a time of generating the new consent document in at least one of the plurality of locations.

3. The method of claim 1, wherein tracking changes to the machine actionable set of rules includes dynamically tracking changes in restrictions regarding what can be done to the specimen and/or whether the patient withdraws consent.

4. The method of claim 3, wherein dynamically tracking changes in restrictions includes providing rule-based querying for specific consent profiles.

5. The method of claim 3, wherein dynamically tracking changes in restrictions includes providing a risk assessment from a consent perspective.

6. The method of claim 1, wherein automatically generating, by the server, the new consent document includes generating the new consent document based on an outline of desired consent, categories of consent needed, and regulations in at least one of the plurality of locations.

7. The method of claim 1, wherein the map includes filters operable to provide interactive visualization of different risk categories.

8. A system comprising:
   a machine-learning regulatory intelligence knowledgebase (RIK), wherein the machine-learning RIK includes global regulations data derived from proprietary and public sources; and
   a server with a processor and a non-transitory memory configured to:
      codify a pre-existing informed consent document into a machine actionable set of rules using machine-learning, natural language processing, and expert assessment, wherein the machine actionable set of rules defines what a patient has consented to be done with a specimen and data derived from the specimen in at least some of a plurality of locations;
      store within the non-transitory memory, the machine actionable set of rules with the specimen;
      track changes to the machine actionable set of rules;
      automatically generate a new consent document based at least in part on global regulations data derived from proprietary and public sources, by using the machine actionable set of rules with any changes and the machine-learning RIK, wherein the machine-learning RIK includes the global regulations data; and
      interactively display visual risk indicators for collection of the specimen as visually corresponding to the plurality of locations on a map.

9. The system of claim 8, wherein the codifying is linked to and performed based upon prevailing global, country, regional, and local regulations in force at a time of generating the new consent document in at least one of the plurality of locations.

10. The system of claim 8, wherein automatically generating the new consent document includes generating the consent document based on an outline of desired consent, categories of consent needed, and regulations in at least one of the plurality of locations.

11. The system of claim 8, wherein tracking changes to the machine actionable set of rules includes dynamically tracking changes in restrictions regarding what can be done to the specimen and/or whether the patient withdraws consent.

12. The system of claim 8, wherein the map includes filters operable to provide interactive visualization of different risk categories.

* * * * *